US008530185B2

(12) United States Patent
Ramasubramanian

(10) Patent No.: US 8,530,185 B2
(45) Date of Patent: Sep. 10, 2013

(54) METHODS AND DEVICES FOR MICROENCAPSULATION OF CELLS

(76) Inventor: Melur Krishnamurthy Ramasubramanian, Vienna, VA (US)

( * ) Notice: Subject to any disclaimer, the term of this patent is extended or adjusted under 35 U.S.C. 154(b) by 885 days.

(21) Appl. No.: 12/337,829

(22) Filed: Dec. 18, 2008

(65) Prior Publication Data
US 2009/0098628 A1   Apr. 16, 2009

Related U.S. Application Data

(62) Division of application No. 11/031,789, filed on Jan. 7, 2005, now Pat. No. 7,482,152.

(60) Provisional application No. 60/534,919, filed on Jan. 8, 2004.

(51) Int. Cl.
| | |
|---|---|
| C12M 1/00 | (2006.01) |
| C12N 11/00 | (2006.01) |
| C12N 11/16 | (2006.01) |
| C12N 5/00 | (2006.01) |
| C12N 5/02 | (2006.01) |
| G01N 1/30 | (2006.01) |
| G01N 33/48 | (2006.01) |

(52) U.S. Cl.
USPC ............... 435/40.51; 435/174; 435/283.1; 435/383

(58) Field of Classification Search
None
See application file for complete search history.

(56) References Cited

U.S. PATENT DOCUMENTS

| | | | | |
|---|---|---|---|---|
| 4,393,133 | A | 7/1983 | Knowles et al. | |
| 5,296,274 | A | 3/1994 | Movchan et al. | 427/566 |
| 5,639,467 | A | 6/1997 | Dorian et al. | |
| 6,365,385 | B1 | 4/2002 | Opara | |
| 6,446,878 | B1 | 9/2002 | Chandra et al. | |

OTHER PUBLICATIONS

International Search Report and Written Opinion of the International Searching Authority for International Patent Application No. PCT/US2005/000391 mailed on Oct. 24, 2005.
Kampf "The Use of Polymers for Coating of Cells" *Polymers for Advanced Technologies* 13: 896-905 (2002).
Chang et al. "Microencapsulation of Living Cells" *NTIS Tech Notes* p. 103 (Jan. 1990).
Briššová et al. "Evaluation of Microcapsule Permeability via Inverse Size Exclusion Chromotography" *Analytical Biochemistry* 242: 104-111 (1996).
Darrable et al. "Durability of Sodium Sulfate-Treated Polylysine-Alginate Microcapsules" *Journal of Biomedical Materials Research* 54(3): 396-399 (2000).
De Vos "Upscaling the Production of Microencapsulated Pancreatic Islets" *Biomaterials* 18(16): 1085-1090 (1997).
De Vos et al. "Factors Influencing Functional Survival of Microencapsulated Islet Grafts" *Cell Transplant* 13(5): 515-24 (2004) Abstract.
De Vos et al. "Association Between Capsule Diameter, Adequacy of Encapsulation, and Survival of Microencapsulated Rat Islet Allografts" *Transplantation* 62(7): 893-899 (1996).
De Vos et al. "Considerations for Successful Transplantation of Encapsulated Pancreatic Islets" *Diabetologia* 45: 159-173 (2002).
De Vos et al. "Factors Influencing the Adequacy of Microencapsulation of Rat Pancreatic Islets" *Transplantation* 62(7): 888-893 (1996).
De Vos et al. "Why Do Microencapsulated Islet Grafts Fail in the Absence of Fibrotic Overgrowth" *Diabetes* 48: 1381-1388 (1999).
Garfinkel, et al. "Optimization of the Microencapsulated Islet for Transplantation" *Journal of Surgical Research* 76: 7-10 (1998).
Hobbs et al. "Prevention of the Morphological changes in Alginate Microcapsules for Islet Xenotransplantation" *Journal of Investigative Medicine* 49(6): 572-575 (2001).
Hsu et al. "The Use of Field Effects to Generate Calcium Alginate Microspheres and Its Application in Cell Transplantation" J Formos Med Assoc 93(3): 240-245 (1994) Abstract.
Lanza et al. "Transplantation of Encapsulated Cells and Tissues" *Surgery* 121(1): 1-9 (1997).
Lanza et al. "Xenotransplantation of Cells Using Biodegradable Microcapsules" *Transplantation* 67(8): 1105-1111 (1999).
Leblond et al. "Quantitative Method for the Evaluation of Biomicrocapsule Resistance to Mechanical Stress" *Biomaterials* 17: 2097-2102 (1996).
Leblond et al. "Studies on Smaller (-315 mM) Microcapsules: IV. Feasibility and Safety of Intrahepatic Implantations of Small Alginate Poly-L-Lysine Microcapsules" *Cell Transplantation* B: 327-337 (1999) Abstract.
Lim and Sun "Microencapsulated Islets as Bioartificial Endocrine Pancreas" *Science* 210(4472): 908-910 (1980).
Opara "The Therapeutic Potential of Islet Cell Transplant in the Treatment of Diabetes" *Exp Opin Invest Drugs* 7(5): 785-795 (1998).
Opara & Kendall Jr. "Immunoisolation Techniques for Islet Cell Transplantation" *Expert Opinion Biological Therapy* 2(5): 503-511 (2002).
Rakowski "Non-Traditional Methods for Making Small Holes: Consider these Alternatives When Conventional Drilling Can't do the Job" *MMS Online* http://www.mmsonline.com/articles/060202.html (2002).
Riss and Moravec "Comparison of MMT, XTT, and a Novel Tetrazolium Compound for MTS for In-Vitro Proliferation and Chemosensitivity Assays" *Mol Biol Cell* 3(Suppl): 184a (1992) Abstract.
Smidsrød and Skják-Bræk "Alginate as Immobilization Matrix for Cells" *TIBTECH* 8: 71-78 (1990).
Soon-Shiong et al. "Insulin Independence in Type 1 Diabetic Patient After Encapsulated Islet Transplantation" *Lancet* 343: 950-951 (1994).

(Continued)

Primary Examiner — Debbie K Ware
(74) Attorney, Agent, or Firm — Myers Bigel Sibley & Sajovec, PA

(57) ABSTRACT

Devices for the microencapsulation of cells include a first chamber for containing a cell-solution suspension. A plate covers one end of the first chamber. The plate has a plurality of apertures. A second chamber is provided for receiving encapsulated cells. The second chamber is separated from the first chamber by the plate. Cells from the first chamber are encapsulated by passing through the apertures in the plate and into the second chamber when pressure is applied to the cell-solution suspension.

20 Claims, 7 Drawing Sheets

(56) References Cited

OTHER PUBLICATIONS

Sun et al. "Injectable Microencapsulated Islet Cells as a Bioartificial Pancreas" *Applied Biochemistry and Biotechnology* 10: 87-99 (1984).

Sun et al. "Normalization of Diabetes in Spontaneously Diabetic Cynomologus Monkeys by Xenografts of Microencapsulated Porcine Islets Without Immunosuppression" *J. Clin. Invest.* 98(6): 1417-1422 (1996).

Uludag et al. "Technology of Mammalian Cell Encapsulation" *Advanced Drug Delivery Reviews* 42: 29-64 (2000).

Van Schitfgaarde and De Vos actors "Factors Influencing the Properties and Performance of Microcapsules for Immunoprotection of Pancreatic Islets" *J. Mol. Med.* 77: 199-205 (1999).

Wolters et al. "A Versatile Alginate Droplet Generator Applicable for Microencapsulation of Pancreatic Islets" *J Appl Biomat* 3: 281-286 (1992) Abstract.

METHODS AND DEVICES FOR MICROENCAPSULATION OF CELLS

RELATED APPLICATIONS

This application is a divisional of U.S. application Ser. No. 11/031,789, filed Jan. 7, 2005 now U.S. Pat. No. 7,482,152, which claims the benefit of priority to U.S. Provisional Application Ser. No. 60/534,919, entitled, "Methods and Devices for Microencapsulation of Cells" filed Jan. 8, 2004, the disclosures of which are hereby incorporated herein by reference in their entirety.

BACKGROUND OF THE INVENTION

The present invention relates to the field of microencapsulation of cells, and more specifically, to the production of microencapsulated cells.

Microencapsulation is an immunoisolation technique available for immunoprotection of cells to be transplanted, which reduces or eliminates the use of immunosuppressive drugs. Uludag H, De Vos P. Tresco P A: *Technology of mammalian cell encapsulation*. Adv Drug Delivery Rev 42: 29-64, 2000. Although, microencapsulation as a viable procedure to immunoisolate cells for transplantation was introduced more than twenty years ago (Lim F, Sun A M. *Microencapsulated islets as bioartificial endocrine pancreas*. Science 210: 908-910, 1980), it has had a slow progress towards clinical application, for example, due to slow production rates and the appearance of fibrotic overgrowths around the capsules, which can result in endotoxin contamination, e.g., oxygen and nutrient deprivation of the enclosed cells.

One of the many prospective applications of this technology is the development of a reliable bioartificial liver in the form of encapsulated hepatocytes, for providing temporary but adequate metabolic support to allow spontaneous liver regeneration, or as a bridge to orthotopic liver transplantation for patients with fulminant hepatic failure. Joly A, Desjardins J-F, Fredmond B, et al. *Survival, proliferation, and functions of porcine hepatocytes encapsulated in coated alginate beads: a step toward a reliable bioartificial liver*. Transplantation 63: 795-803, 1997.

Examples of devices for microencapsulation include the air-syringe pump droplet generator (Wolters G H, Fritschy W M, Gerrits D, Van Schilfgaarde R: *A versatile alginate droplet generator applicable for microencapsulation of pancreatic islets*. J Appl Biomat 3: 281-286, 1992) and the electrostatic bead generator (Hsu BR-S, Chen H-C, Eu S—H, Huang Y-Y, Huang H-S: *The use of field effects to generate calcium alginate microspheres and its application in cell transplantation*. J Formos Med Assoc 93: 240-245, 1994). Each of these devices is fitted with a single needle through which droplets of cells suspended in alginate solution are produced and cross-linked into spherical beads. Various methods for the production of encapsulated cells in increased numbers have been attempted, including the simultaneous production of multiple droplets in a multiple needle approach (De Vos P, De Haan B J, Schilfgaarde R. *Upscaling the production of microencapsulated pancreatic islets*. Biomaterials 18: 1085-1090, 1997) or increasing the number of cells/mL of alginate suspension in the syringe to increase the probability of the formation of encapsulated cells. However, air-syringe pump droplet generators or electrostatic bead generators may be incapable of producing sufficient numbers of microcapsules in a short-time period to permit mass production of encapsulated and viable cells for transplantation in large animals and humans. Moreover, a prolonged process of encapsulation of cells may adversely affect the viability of the cells.

For example, in a study with four nozzles, the nozzles are fitted to a header plate where in the cell in alginate is supplied and pushed through four hypodermic needles. De Vos P, De Haan B J, Schilfgaarde R. *Upscaling the production of microencapsulated pancreatic islets*. Biomaterials 18: 1085-1090, 1997. However, this may not be scaled up effectively because of the support mass surrounding the hypodermic needle such as couplings and seals, which provides a spacing of about 1 cm between needles. An increase in the number of joints in the flow path through which the cell-alginate suspension travels may result in a higher the possibility of stagnation, clogging, and contamination. Furthermore, alginate solutions used for encapsulation are viscous, making the process potentially fraught with the risk of clogging when small gauge needles are used to produce microcapsules of desirable size range (e.g., <800 microns in diameter). When needle clogging occurs, the process of unclogging the needle for resumption of encapsulation further increases the duration of microencapsulation of large batches of cells for therapeutic use. High density of parallel needles may not provide the access needed to clean clogged needles in the center of the array in a fairly dense grid. Multiple needles with a common flow header may not be viable and/or efficient.

Even using such an approach, production rates at several orders of magnitude higher may be desirable to meaningfully produce sufficient quantities of encapsulated and viable cells for transplantation in human subjects. For example, it has been estimated that for the 1 million islets needed for transplantation in a diabetic human subject, about 100 hours may be required to complete the encapsulation of this number of islets, assuming one islet/microcapsule and a single needle operation. However, in practice, it has actually been estimated that the duration of the process may be closer to 200 hours because of the additional steps involved in the encapsulation procedure, following the generation of the initial cell-containing alginate microspheres.

Moreover, it has been reported that by using the syringe method, the proportion of spheres that contain cells is only about 50%. Attempts may be made to increase the concentration of cells in the alginate suspension to increase the chance process of encapsulating a cell and thereby increasing the productivity. However, this may provide only a two-fold increase in productivity. Further, an increase in the number of cells/mL alginate could cause an increase in the number of beads of cells with imperfections, such as cell protrusion into the bead membrane. Protrusion of encapsulated tissue through the microcapsule membrane may activate the cell-mediated host immune response leading to microcapsule transplant rejection. Sun A M. O'Shea G M. Goosen M F: *Injectable microencapsulated islet cells as a bioartificial pancreas*. Appl Biochem Bioteclnol 10: 87-99, 1984.

SUMMARY OF THE INVENTION

Embodiments of the present invention provide methods, systems and devices for the microencapsulation of cells. In some embodiments, a first chamber is provided for containing a cell-solution suspension. A plate covers one end of the first chamber. The plate has a plurality of apertures. A second chamber is provided for receiving encapsulated cells. The second chamber is separated from the first chamber by the plate. Cells from the first chamber are encapsulated by passing through the apertures in the plate and into the second chamber when pressure is applied to the cell-solution suspension.

In other embodiments, method for the microencapsulation of cells include providing a cell-solution suspension in a first chamber having a plate covering one end, the plate comprising a plurality of apertures and forcing the cell-solution suspension through the apertures in the plate into a second chamber.

DETAILED DESCRIPTION OF THE INVENTION

The present invention now will be described more fully hereinafter with reference to the accompanying drawings, in which illustrative embodiments of the invention are shown. This invention, however, should not be construed as limited to the embodiments set forth herein; rather, these embodiments are provided so that this disclosure will be thorough and complete, and will fully convey the scope of the invention to those skilled in the art.

Embodiments of the invention provide methods and systems for the microencapsulated of cells. The microencapsulation of cells includes techniques designed to entrap viable cells within the confines of semi-permeable membranes that are permeable to small molecules, such as nutrients and oxygen, which are essential for cell survival, but impermeable to large molecules, such as antibodies and immune cells. Such techniques may be of interest in cell therapy for a variety of pathophysiologic conditions, including anemia, dwarfism, kidney failure, liver failure, pituitary and CNS insufficiencies, and diabetes mellitus. However, other applications of encapsulated cell technology besides cell transplantation are possible. Uludag H, De Vos P, Tresco P A: *Technology of mammalian cell encapsulation*. Adv Drug Delivery Rev 42: 29-64, 2000. Other applications of encapsulated cell technology can include the large-scale production of cell-derived molecules in biotechnology, clonal selection of desired cell phenotypes, the in vitro cultures of cells dependent on close cell-cell contact, in vivo cell cultures, reproductive technology, and cytotoxicity testing.

Examples of encapsulated cells include cells encapsulated within alginate spheres that are ionically crosslinked (gelled) with Ca++ to immobilize living cells. Capsules within the diameter range of 0.05-1.5 mm are generally referred to as microcapsules. As discussed herein, the success of the cell microencapsulatioln technique can be determined by the evaluation of the capsule properties, and the function of the encapsulated cells. Smiidsrod O, Skjak-Braek G: *Alginiate as immobilization matrix for cells*. Trends Biotechnol 8 (3): 71-78, 1990. Opara E C, Kendall W F. *Immunoisolation techniques for islet cell transplantation*. Expert Opin Biol Therapy 2: 503-511, 2002.

Figure 1:
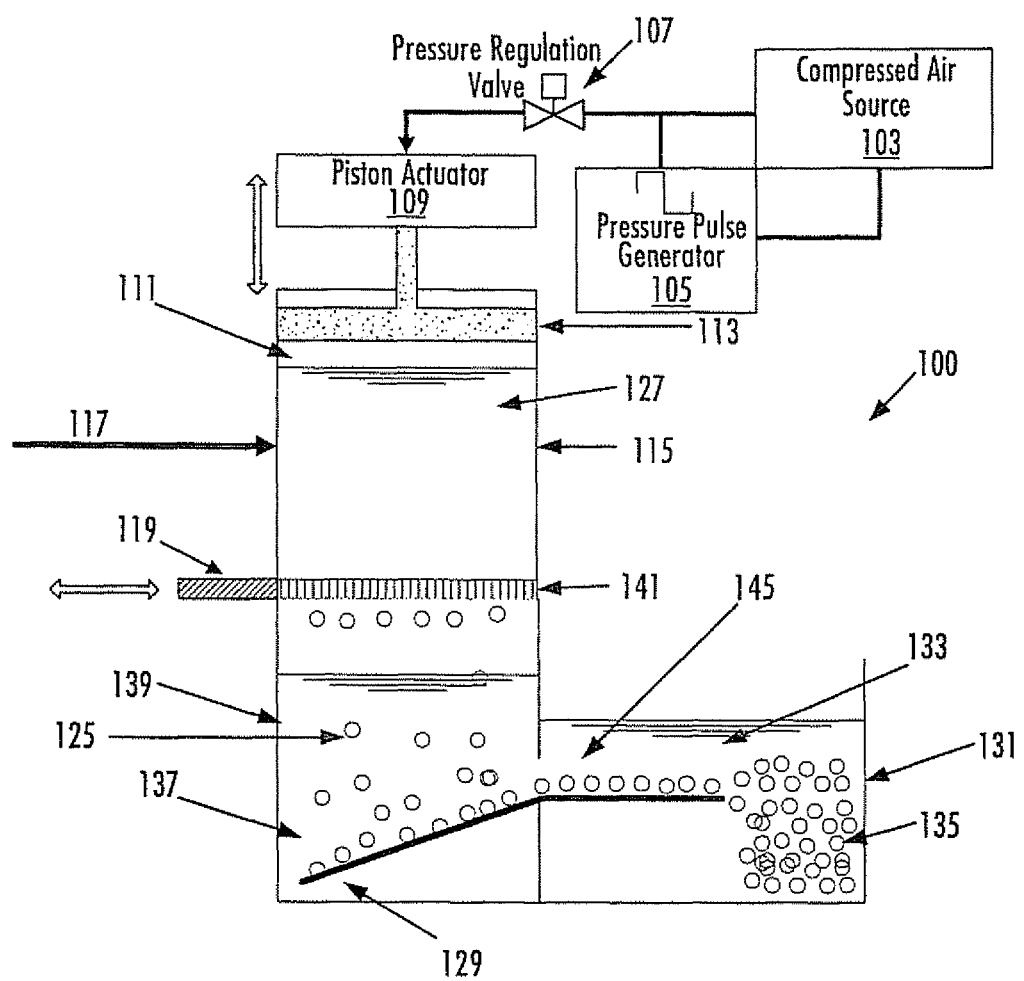
FIG. 1 is a schematic drawing of a cell encapsulation device according to embodiments of the invention.

As shown in FIG. 1, a device 100 for the microencapsulation of cells includes a pre-encapsulation tank 115 and a post-encapsulation tank 139 separated by a perforated plate 141. The pre-encapsulation tank 115 includes a cell/solution suspension 127 that contains the cells that are to be encapsulated, such as Hep G2 cells, suspended in an encapsulation solution, such as alginate. The post-encapsulation tank 139 includes a post-encapsulation solution 137, such as a calcium chloride solution, that can facilitate the cross-linking of the encapsulation solution around the cells.

In summary, pressure is exerted on the cell/solution suspension 127 to force the suspension 127 through the apertures in the perforated plate 141 to produce encapsulated cells 125. The generated microencapsulated cells 125 are received in the post-encapsulation tank 139 and proceed to the solution 137, which facilitates cross-linking of the encapsulation material.

Although embodiments of the present invention are described herein with respect to the microencapsulation of Hep G2 cells in an alginate solution, other cells and solutions can be used. For example, normal hepatocytes may be encapsulated for use as a bioartificial liver. Parenchymal hepatocytes may also be isolated from live animals and subsequently encapsulated. Other encapsulated cells include islets, pituitary, and adrenal cells. The Hep G2 is a single cell line derived from human hepatocellular carcinoma. Ultrapurified low viscosity high-mannuronic acid alginate (UPA) with low endotoxin content may also be obtained from Pronova/FMC (Philadelphia, Pa.). Hep G2 produces the regular biological macromolecules such as albumin, alpha-fetoprotein, apo-transferrin, alpha2-macroglobulin, haptoglobin, ceruloplasmin, fibrinogen, plasminogen, complement (C3, C4), and a host of other proteins normally produced by parenchymal hepatocytes (U.S. Pat. No. 4,393,133), and may be a good model of hepatocytes. Therefore, the mass production of encapsulated Hep G2 cells may provide a valid basis for the development of a bioartificial liver system involving the use of isolated normal hepatocytes.

As described herein, the viability of encapsulated cells can be assessed using molecular probes to determine cell viability and proliferation, and metabolic techniques may be used to assess cell function. The function of encapsulated cells can be compared with that of unencapsulated cells. In addition, ELISA assays can be used to determine the identity of specific proteins (albumin, transferrin, and a-fetoprotein) synthesized and exported to the exterior by encapsulated cells. Biomaterials for encapsulation can be compared for biocompatibility, mechanical strength and durability of microcapsules. Based on the evaluation of these parameters of microcapsule properties, appropriate adjustments may be made in the microencapsulation procedure to adjust for encapsulation material properties, including viscosity, density, and the like. The desired perme-selectivity can be obtained. For example, encapsulation materials may be selected which permit the secretion of large molecular weight proteins (MW>150 Kda) made by encapsulated cells, while preventing the entry of immune cells into the capsules.

With reference to FIG. 1, the perforated plate 141 includes a plurality of apertures that can be drilled, for example, using electron beam drilling techniques, on the surface of the plate 141 adjacent the post-encapsulation tank 139. The apertures can be shaped and positioned in such a way as to facilitate the smooth flow of cell/solution suspension when subjected to pressure. As illustrated in FIG. 1, a piston 113 can be used to exert pressure on the cell/solution suspension 127 to force encapsulated cells through the perforated plate 141. A piston actuator 109 can be in complete contact with the cell/solution suspension 127 and actuated by electromechanical mechanisms with a servo linear actuator and controller that can be programmed to generate the motion amplitude and frequency desired. The piston actuator 109 can be a piezoelectric piston actuator, although other types of actuators and/or configurations can be used to exert pressure on the cell/solution suspension 127. For example, the piston actuator 109 and the piston 113 can be omitted, and the pre-encapsulation tank 115 may be provided with a gasket and seal with a lid with inlet(s) for compressed air entry to exert pressure on the cell/solution suspension 127. A compressed air source 103 regulated by a pressure regulation valve 107 and a pressure pulse generator 105 can apply force to the cell/solution suspension 127. A compressed air space 111 may be provided to exert pressure on the cell/solution suspension 127.

In some embodiments, the level of the cell/solution suspension 127 is maintained using a non-contact ultrasonic level sensor placed inside the lid of the pre-encapsulation tank 115 or the piston 113. The flow of solution and cells through the inlet 117 can be controlled with the level signal feedback. Compressed air in the compressed air space 111 can be used to provide additional space to pressurize the cell/solution suspension 127 and/or to force the cell/solution suspension 127 through the holes in the bottom of the vessel. The air cushion in the compressed air space 111 above the cell/solution suspension 127 may be pulsated, for example, using the pressure pulse generator 105, to control the droplet formation by preventing a continuous stream of fluid through the holes. The pulsed pressure can be applied to produce uniform-sized encapsulated cells 125. Such pulsed pressure from a compressed air source 103 may be applied without requiring the piston 113. Moreover, aggressive pressure relief may not be necessary for successful microencapsulation production.

The air space 111 can be reduced or eliminated and the pressurization of the cell/solution suspension 127 maintained by creating pressure pulses using the piston actuator 109, such as a piezoelectric transducer, to drive the piston 113 from the top using high forces and small displacement.

With continued reference to FIG. 1, an inlet 117 is provided can be used for the entry of the solution and the cells into the pre-encapsulation tank 115. For example, the inlet 117 can include high-pressure valve entries for a supply of solution, such as alginate, and a supply of cells suspended in a suitable medium, such as saline, Peristaltic pumps and/or Moyno cavity pumps can be used to pump the solution into the pre-encapsulation tank through the inlet 117. Peristaltic and/or Moyno cavity pumps may be used to impart low shear stress to the conveyed fluid, and can also provide a controlled, sterile environment. These pumps may also handle pure liquids, including viscous and non-viscous to viscous fluids with suspended solids.

Planar vibratory motion may be provided to the plate 141 to facilitate drop release and produce a steady stream of microencapsulated cells 125. The planar vibratory motion can be provided by a plate actuator 119, such as a piezoelectric actuator, that is coupled to the plate 141 as shown in FIG. 1. Any suitable agitation mechanism may be used to prevent the settling of cells at the bottom of the tank and to maintain uniform distribution of cells in the cell/solution suspension 127, including a large slowly rotating agitator for bulk movement and/or smaller high speed mixers for imparting high shear stresses in a localized area to break up clusters of cells.

In some embodiments, a continuous production mode can be provided such that a suitable "bead elevator," such as conveyor 129, is used to transport cross linked microencapsulated cells 125 and transfer the cells 125 to a holding tank 131 that contains a wash solution 133 in a continuous fashion. The configuration of the conveyor 129 may be selected so that the beads reside in the solution 137 in the post-encapsulation tank 139 for the required cross-linking time. For example, cross-linking can require between about 5 and about 15 minutes. In some embodiments, post-encapsulation solution 139 flows under the perforated plate 141 so that the beads continue to move during the required gelling time before being elevated out of the cross linking bath.

As illustrated, the inclined conveyor 129 has a flexible surface immersed in the post-encapsulation tank 139 that moves continuously to carry the encapsulated cells 125 from the bottom of the conveyor 129 and finishing at the top of the conveyor 129 after the desired cross-linking time. However, other configurations, such as horizontal conveyors, can also be used. The surface of the conveyor 129 can contain fully cross-linked encapsulated cells 125 that can be removed by light suction through an opening 145 into the holding tank 131. The encapsulated cells 125 are stored in a collection area 135 of the holding tank 131 in the wash solution 133. The wash solution 133 can be a saline bath.

In other embodiments, the holding tank 131 and conveyor 129 may be omitted and the encapsulated cells 125 can be produced in a batch mode.

After the formation of microencapsulated cells, various solutions may be applied to provide additional layers to the microencapsulated cell. For example, the microencapsulated cells can be coated with poly-L-lysine or Polyornithine, followed by an outer coating with alginate to form a semipermeable membrane around the initial encapsulated core, which may be an alginate core. Further, the core alginate may be reliquified by chelation with sodium citrate solution.

In some embodiments, the various tanks 115, 139, and 131 can be made of smooth 316-stainless steel cylindrical vessel. The flat perforated plate 141 can be either integral to one or more of the tanks 115, 139, or 131 or can be provided as a separate attachment. The inner diameter of the various tanks 115, 139, and/or 131 can be about 3.5-inches (88.9 mm) and have a wall thickness of about ¼-inch (6.35 mm). Holes can be drilled using electron beam drilling techniques at the bottom of the pre-encapsulation tank 115 or in a separately provided plate 141. Various micro-drilling processes can be used, including non-traditional processes. For example, Electron Discharge Micromachining (EDM), laser micro-drilling, and electron beam drilling can be used. By way of example, in certain filter applications, 6 million holes each having a 0.006-in diameter were drilled in a stainless steel disk 24 inches in diameter and 0.125-in thick.

Various parameters may be adjusted to control aspects of the generation of the microencapsulated cells. For example, the geometry of the apertures in the plate 141 can be selected to generate microencapsulated cells of a certain shape or size.

Figure 2:
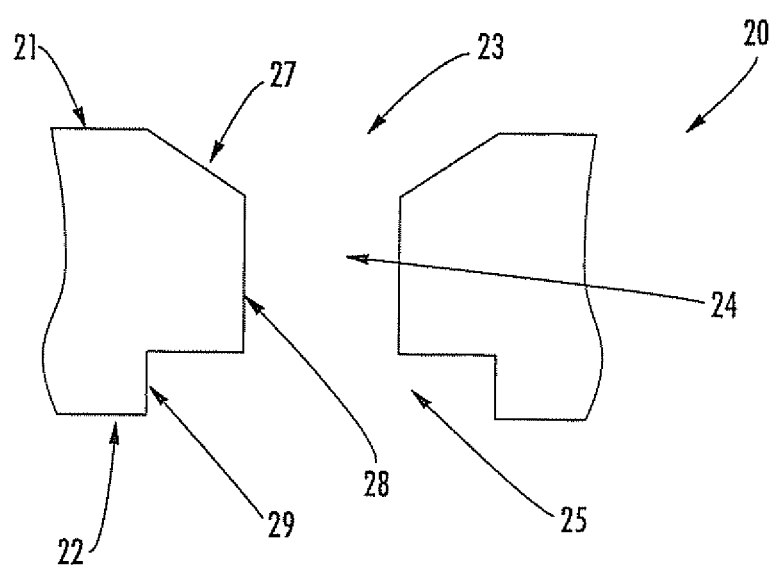
FIG. 2 is a cross sectional side view illustrating a perforation for encapsulating a cell according to embodiments of the invention.
Figure 3:
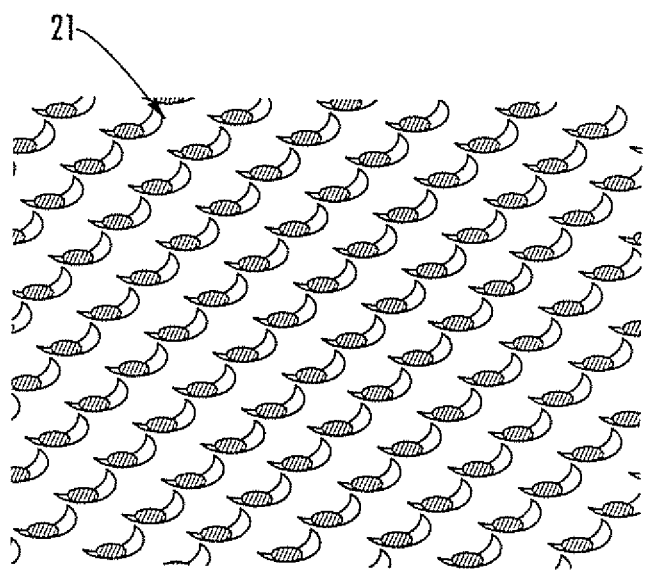
FIGS. 3 and 4 are perspective views of a perforated plate for encapsulating cells according to embodiments of the invention.
Figure 4:
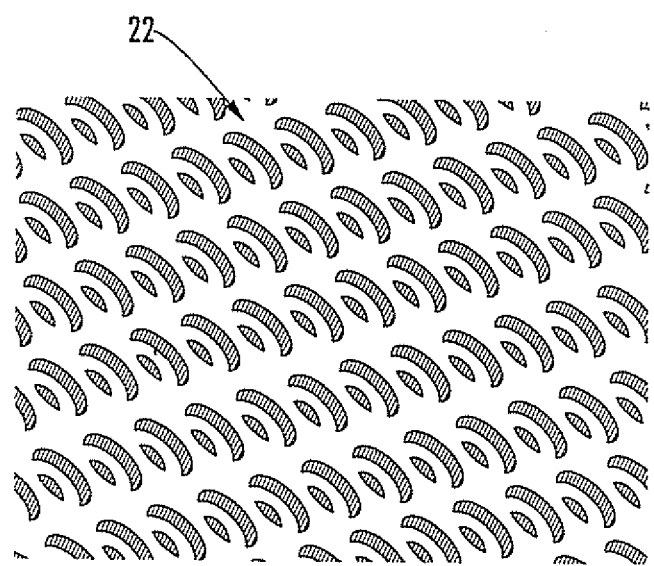

An cross sectional side view of an exemplary aperture 20 that can be formed in plate 141 is shown in FIG. 2. The aperture 20 has a top surface 21 that is adjacent the pre-encapsulation tank 115 in FIG. 1 and a bottom surface 22 that is adjacent the post-encapsulation tank 139. With reference to FIG. 2, the top surface 21 has an inlet 23 with a contoured edge 27 for receiving the cell/solution suspension 127 (FIG. 1). The bottom surface 22 includes an outlet 25 with a straight edge 29 that is connected to the inlet 23 via a straight portion 24. An expanded view of the top surface 21 and the bottom surface 22 is provided in FIGS. 3 and 4. As shown in FIG. 2, the aperture 20 is sized so that a cell and a desired amount of solution (e.g., alginate solution) can be forced through the inlet 23 around the contoured edge 27 and though the straight portion 24 such that a microencapsulated cell is formed and ejected through the outlet 25.

Accordingly, various parameters of the aperture 20 shown in FIG. 2 may be adjusted responsive to the size of the cells and/or the size of the encapsulated material that is desired, such as the shaped of the contoured edge 27, the size of the inlet 23, the length of the straight portion 24, the size of the outlet 25, and the shape of the outlet edge 29. For example, the inlet 23 and/or the outlet 25 can provide a greater cross-sectional area than the channel straight portion 24.

In some embodiments, the aperture 20 has an inlet 23 cross-section of about a 0.5 mm in diameter, a tapered conical section along the contoured edge 27 through the first approximately 0.5 mm of depth, followed by the straight portion 24 having a length of between about 1 mm and 3 mm and having the required diameter to produce a desired droplet size, and a final flared outlet 25 of 0.5 mm. The diameter of the straight portion 24 can vary based on the size of the cell to be encapsulated. For example, Hep G2 cells are about 20 μm in diameter whereas an islet cell can be as large as 200 μm, or typically between about 70 μm to 200 μm. Accordingly, the diameter of the straight portion 24 should be about 20 μm to about 40 μm for a Hep G2 cell and about 150 μm to about 250 μm for an islet cell. Other configurations are possible. For example, in some embodiments, the straight edge 29 portion of the outlet 25 is omitted and replaced with a contoured or tapered edge.

In some embodiments, holes with a 113 μm diameter in a 0.55 mm thick stainless steel plate are drilled rising electron beam drilling techniques. In some embodiments, a one millimeter diameter envelop per hole is allowed for a single 63.5 mm diameter plate, resulting in nearly 4900 holes. Thus, a large number of encapsulated cells may be produced in parallel.

In addition to the examples given above, between about 3000 to about 5000 apertures may be provided on a plate. Each aperture can have a tapered inlet having a cross-sectional diameter of about 0.5 mm, an outlet having a cross-sectional diameter of about 0.5 mm, and a channel portion connecting the inlet and outlet having a cross-sectional diameter of between about 50 μm and about 500 μm.

Other variable parameters within the scope of the invention arise from device operations. Operational parameters include the viscosity of the cell/solution (e.g., alginate) suspension, the concentration of cells (e.g., Hep G2 cells) in the suspension, the fluid levels of the pre-encapsulation tank 115, the post-encapsulation tank 139, and the holding tank 131 (shown in FIG. 1), the flow rate of solution into the pre-encapsulation tank 115, the internal stirring rates of pre-encapsulation tank stirrers, the air pressure (such as in the compressed air space 111), and the pulsation frequency of the force exerted on the cell/solution suspension 127. For example, the viscosity of the cell/solution (e.g., alginate) suspension can be between about 20 and about 200 mPa·S. The concentration of cells (e.g., Hep G2 cells) in the suspension can be between about 500 and about 10000 cells/ml. The fluid levels of the pre-encapsulation tank 115 can be between about 10% and about 100% of the tank height, the fluid levels in the post-encapsulation tank 139 can be between about 30% and about 80% of the tank height, and the fluid levels in the holding tank 131 can be between about 30% and about 80% of the tank height. The flow rate of solution into the pre-encapsulation tank 115 is between about 0.5 and about 10 liters/min. The internal stirring rate can be between about 1 Hz and about 100 Hz. The air pressure in the compressed air space 111 can be between about 5 kPa and about 600 kPa. The pulsation frequency of the force exerted on the cell/solution suspension 127 can be between about 1 Hz and about 1000 Hz.

Additional parameters relate to the ability of the system to keep the microencapsulated cells or spheres of encapsulation solution (e.g., alginate) exiting from a perforated plate from coalescing, and to prevent the encapsulated cells from drifting away in air. For example, as illustrated in FIG. 1, the spacing from the bottom of the perforated plate 141 to the surface of the solution 137 bath may selected to prevent exiting microencapsulated cells 125 from coalescing or drifting away in air. In some embodiments, the space between the plate 141 and the solution 137 may be closed to minimize the distance from the plate 141 to the top of the solution 137 or a mist of calcium chloride can be maintained immediately below the perforated plate to facilitate cross linking as early as possible. Moreover, the cell-containing microspheres may begin cross-linking soon after leaving the perforations and before they have a chance to drift and cross-interact and possibly coalesce. Thus, it may be desirable to facilitate the direct flow of microencapsulated cells 125 into the bath solution 137 using electrostatic forces. For example, electrostatic forces can be used to pull the droplets away from perforated plat 141. For example, a spray direction can be applied using electrostatic forces by making the pre-encapsulation tank 115 and perforated plate 141 with non-conducting materials and forming a high-voltage electric circuit using cell/solution suspension 127 and the bath solution 137 (e.g., alginate and calcium chloride, respectively).

Optimal conditions can be determined or estimated for the production of spherical beads, such as alginate beads, with minimum variation in shape and size. It may be possible to satisfactorily characterize the device in the generation of empty alginate microspheres prior to producing encapsulated cells. Subsequently, various additional optimal conditions can be determined, including the pre-encapsulation solution/cell ratio, air pressure, and pre-encapsulation solution flow rate for the production of standard size microspheres (diameter range 50-500 μm).

The parameters discussed herein may be studied and systems designed from modeling of flow through variously sized apertures and/or nozzles. For example, modeling software such as FLUENT, a Computational Fluid Dynamics Code (CFD) (Fluent Incorporated Network Services, Lebanon, N.H., U.S.A.) can be used to examine various viscous and two-phase flow capabilities to design the aperture shape. The dimensions for the desired size of microspheres can be selected and the droplet generation process may be simulated. Various parameters such as viscosity, concentration, and spacing between the plate and the post-encapsulation tank solution, e.g., a calcium chloride bath, may also be studied parametrically using a CFD model of the process. Such analysis can be used to design devices according to embodiments of the present invention. The CFD results can be validated experimentally. The manufacturing process can be characterized in terms of production rate and the quality of the microcapsules.

In some embodiments, the surfaces that may contact the cells and suspension solution may be treated or formed to provide a smooth surface and to reduce attraction of the cells to the surfaces. For example, various surfaces that may contact the cells and solution in which the cells are suspended can be coated with a thin layer of diamond-like carbon using chemical vapor deposition or a plasma coating technique to provide a smooth flow of alginate and cells, especially through narrow pathways of the perforated plate. These surfaces can be applied using techniques known to those of skill in the art.

According to embodiments of the present invention, larger numbers of cells encapsulated in microspheres, such as alginate microspheres, may be produced in comparison with conventional techniques. In some embodiments, the rate of production may be increased by about 5000 times or more in comparison with conventional devices described herein. For example, certain conventional devices require 100 or more hours for the production of one million microencapsulated islets for human transplantation. Embodiments of the present invention may reduce the production time of one million microencapsulated islets to less than about two minutes. The entire encapsulation process of one million microencapsulated islets may be completed in less than forty-five minutes, including all the post processing steps, such as the cross-linking residence time of about five to about fifteen minutes, washing times of about three to about five minutes, Poly-Ornithine coating processes with a residence time of about five to about ten minutes followed by washing the encapsulated cells, recoating the encapsulated cells with alginate, and a chelation process to liquefy the core in about ten to about fifteen minutes. Moreover, a reduced production time may result in a positive impact on the viability of the encapsulated cells.

Although embodiments of the present invention have been described with respect to the device shown in FIG. 1, other configurations can be used. The various tanks can be provided as cylinders or other shapes, such as various polyhedrons, cubes, or irregular shapes. For example, higher rates of production may be obtained by additionally perforating a laterally curved surface of a spherical cylinder and pressurizing an enclosed encapsulation solution/cell suspension. The encapsulation solution/cell suspension can be subjected to pulsating pressure at the same time as the cylinder is rotated. The pressure pulsation can be generated by an eccentrically rotating solid cylindrical surface that may produce a narrow nip and a wide region at a pre-determined frequency. The production rate is generally proportional to the length of the cylinder.

Figure 5:
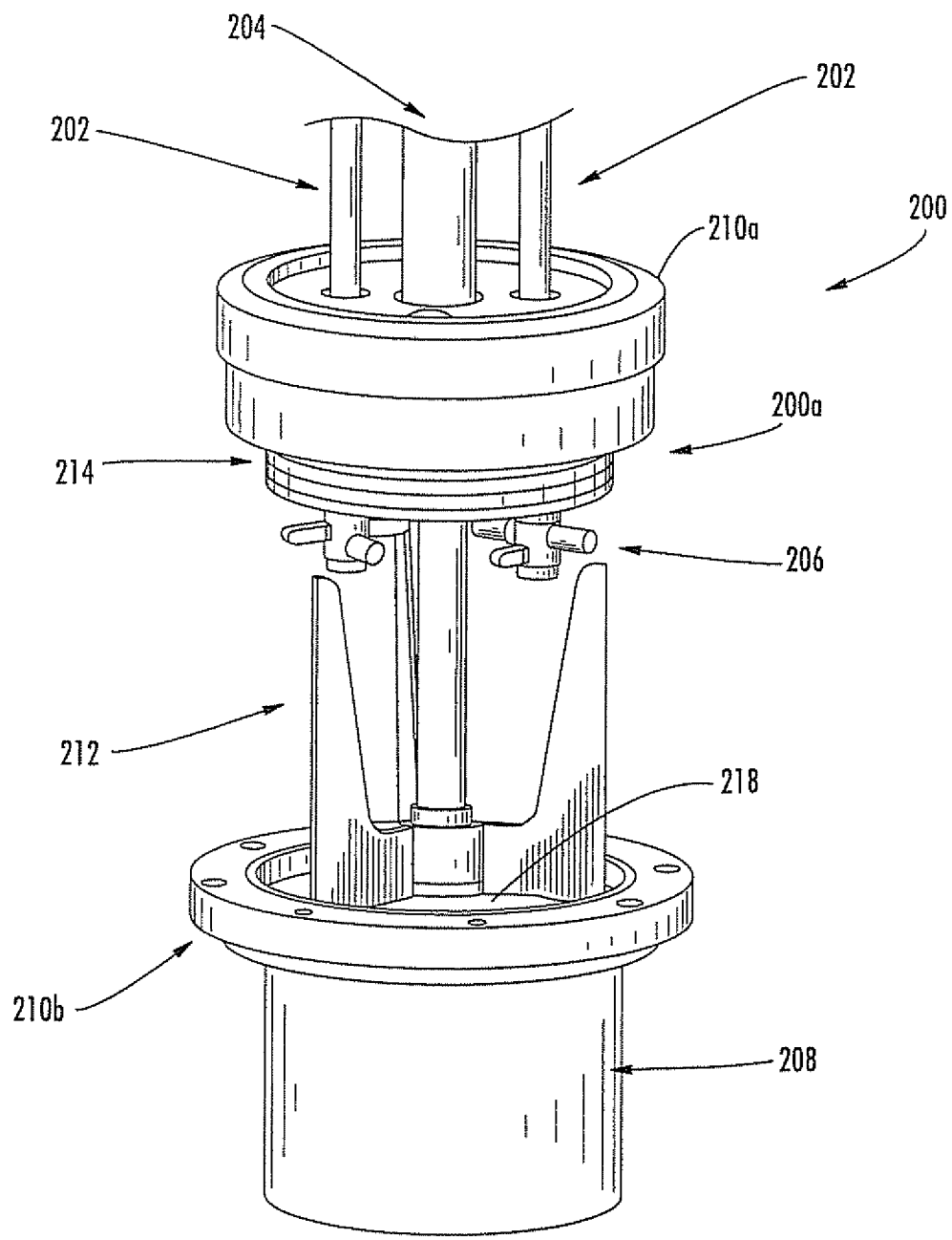
FIGS. 5, 6, and 7 are perspective views of a cell encapsulation device according to further embodiments of the invention.
Figure 6:
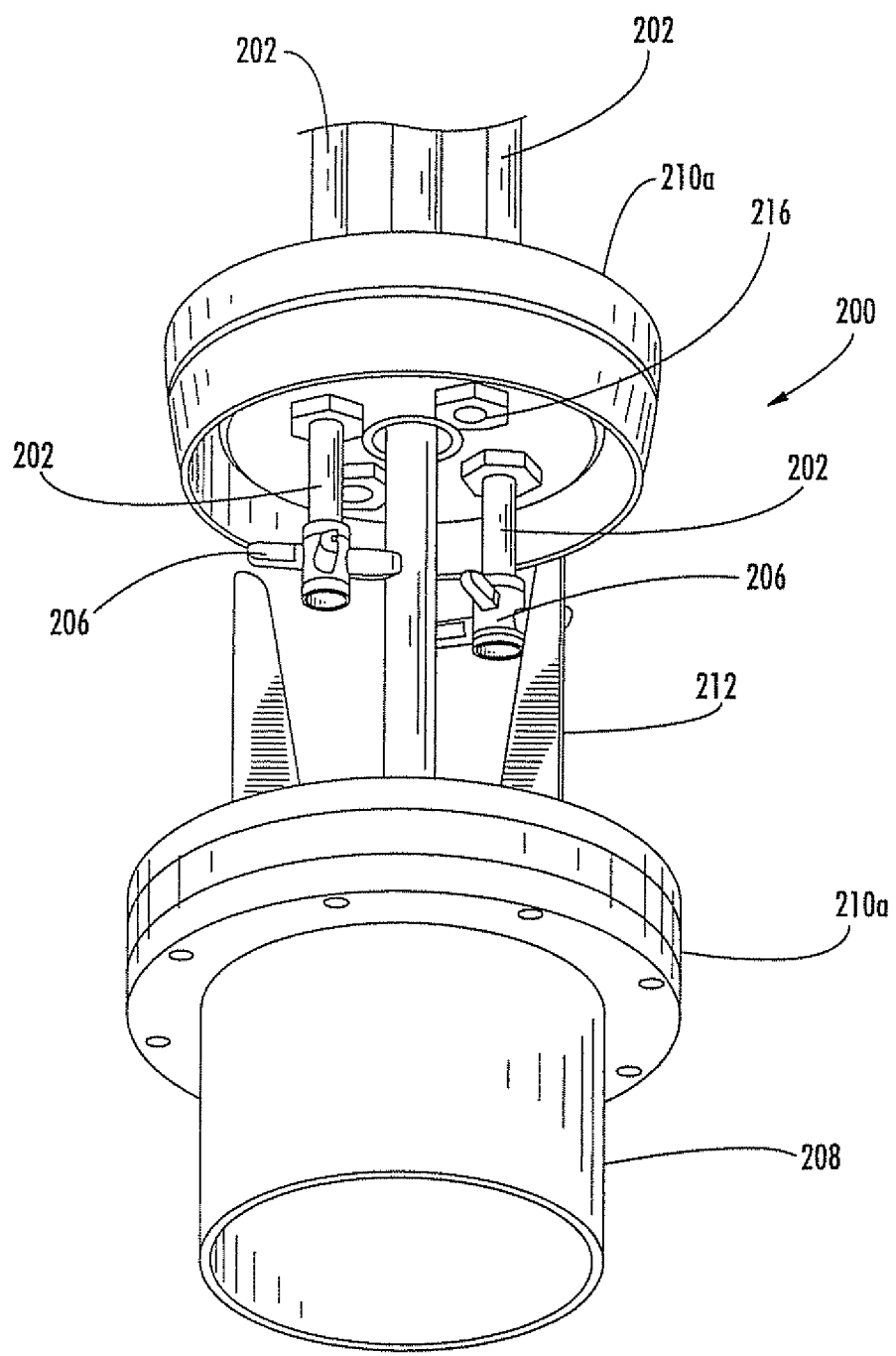
Figure 7:
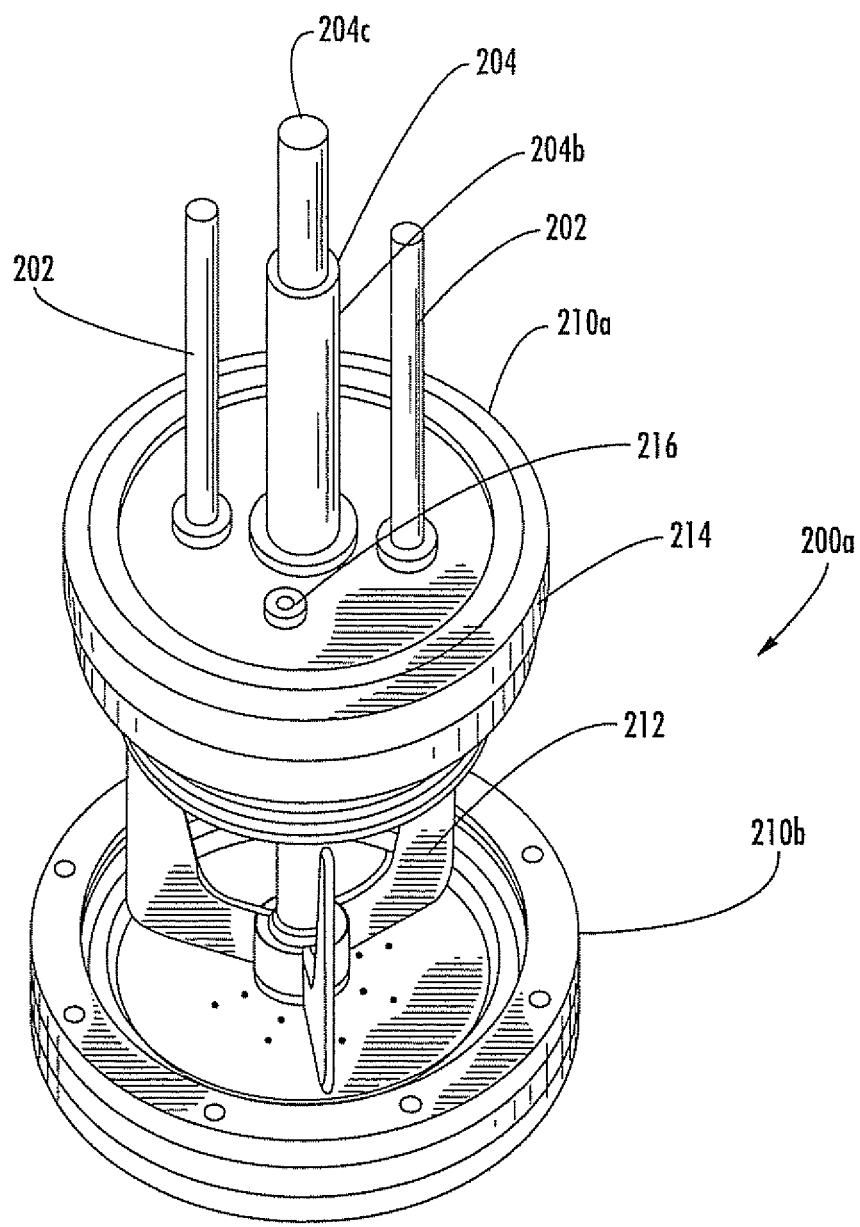

Referring to FIGS. 5 and 6, a device 200 includes a top portion 200a for holding the pre-encapsulation tank (not shown) and a post-encapsulation tank 208. The top portion 200a of the device 200 without the post-encapsulation tank 208 is shown in FIG. 7. The device 200 includes an upper frame 210a that holds a piston 214 for providing pressure to a liquid in the pre-encapsulation tank, a large co-axial shaft 204 for rotating a large agitator 212, and two smaller shafts 202 for rotating two smaller agitators 206. A lower frame 210b holds a perforated plate 218 between the top portion 200a and the post-encapsulation tank 208. The frame 210b can be connected to vibratory actuators for vibrating the perforated plate 218 as described above. The pre-encapsulation tank is not shown for clarity. However, it should be understood that a pre-encapsulation tank can be provided in the region between the upper frame 210a and the lower frame 210b.

As shown in FIG. 7, the co-axial shaft 204 includes an inner portion 204a and an outer portion 204b. The inner shaft 204a is connected to the piston 214 for providing pressure pulsing motion. The outer shaft 204b provides rotational motion to rotate the large agitator 212. The agitator 212 can rotate at a relatively slower speed, and the smaller agitators 206 can rotate at a relatively faster speed. The agitators 206 and 212 agitate the cell/solution suspension so that the cells are more evenly spread throughout the suspension. Clustering of the cells can be reduced. In particular, the agitators 206 can reduce cell clustering on the piston 214.

As illustrated in FIGS. 6 and 7, the piston 214 of FIG. 5 can be removed. Apertures 216 are provided for the introduction and expulsion of air, including compressed air for providing pressure to the cell/solution suspension as discussed above.

Figure 8:
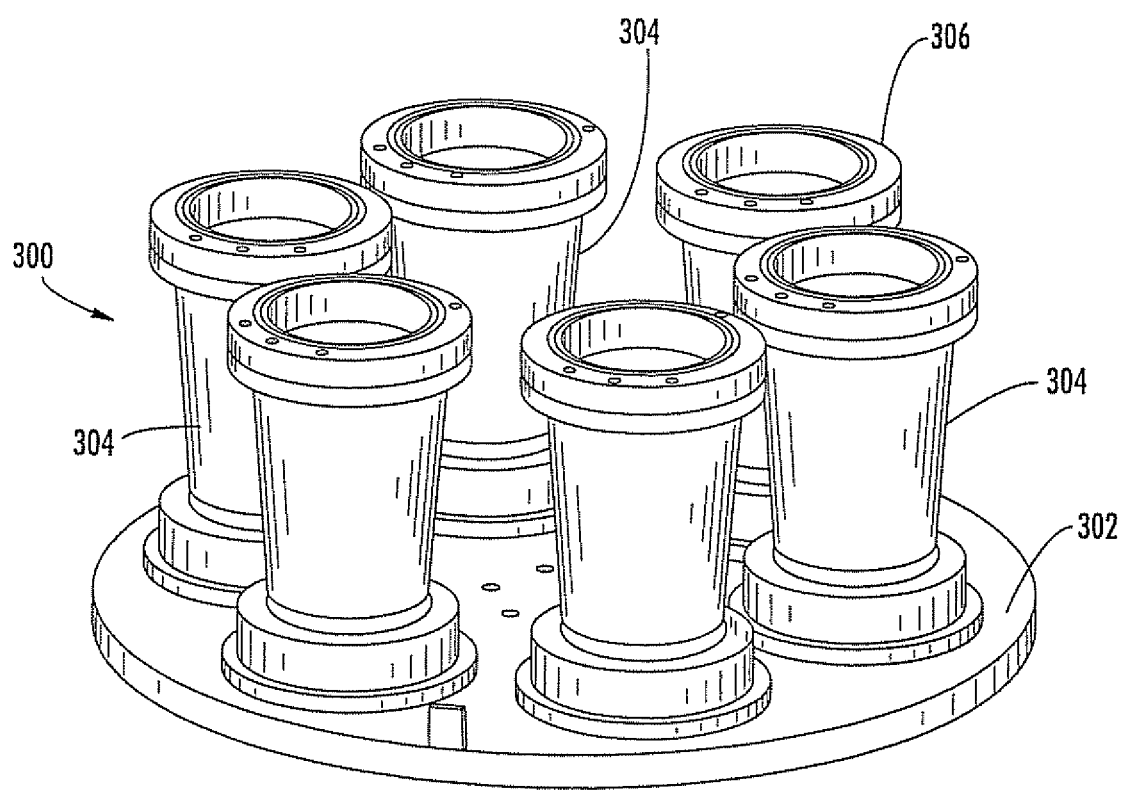
FIG. 8 is a perspective view of a multi-tank device according to further embodiments of the invention.

Another device 300 for use in batch mode processing is shown in FIG. 8. The device 300 includes an indexing plate 302 for holding post-encapsulation tanks 304. One or more of the post-encapsulation tanks 304 can be connected to a pre-encapsulation tank separated by a perforated plate by a flange 306. For example, the pre-encapsulation tank can be the pre-encapsulation tank 208 described in FIGS. 5, 6, and 7.

In some embodiments, a single pre-encapsulation tank is connected to a selected one of the post-encapsulation tanks 304. Cells can then be encapsulated using the encapsulation methods and devices discussed herein. When the selected post-encapsulation tank 304 has received a given amount of encapsulated cells (e.g., the selected tank 304 is full), the plate 302 can be rotated so that the pre-encapsulation tart is connected to another one of the post-encapsulation tanks 304. In some embodiments, the post-encapsulation tanks 304 can be replaced with additional tanks for processing, such as tanks filled with calcium chloride solution. For example, an automated arm can remove and replace tanks 304 that have been filled to some capacity with encapsulated cells. In this configuration, a number of tanks 304 can be filled with encapsulated cells to allow for post-processing time, such as the time that can be needed for cross-linkage, and the production of microencapsulated cells can occur substantially continuously. Other multi-tank configurations can be used. For example, the post-encapsulation tanks 304 can be provided on a linear conveyor belt.

According to embodiments of the present invention, microspheres and/or microencapsulated cells can be produced with minimum variation in shape and size. Optimal conditions can be determined as discussed herein, including the alginate/cell ratio, air-jacket pressure (e.g., the pressure of the compressed air space 111 shown in FIG. 1), and alginate flow rate for the production of standard size (diameters 300-500 µm, preferably smaller) spherical alginate microcapsules containing Hep G2 cells. The size of the microcapsules may be controlled. For example, larger capsules may be associated with increased cell death owing to impaired diffusion of nutrients and oxygen to the cells at the center of the capsule interior. Also, the size of microcapsules may have an impact on the kinetics of the release of products from encapsulated cells. Opara E C, Kendall W F. *Immunoisolation techniques for islet cell transplantation*. Expert Opin Biol Therapy 2: 503-511, 2002. However, the incidence of inadequate encapsulation can be inversely proportional to the capsule diameter. De Vos P, Hamel A F, Tatarkiewicz K: *Considerations for successful transplantation of encapsulated pancreatic islets*. Diabetologia 45: 159-173, 2002. Van Schilfgaarde R, De Vos P: *Factors influencing the properties and performance of microcapsules for immunoprotection of pancreatic islets*. J Mol Med 77: 199-205, 1999. An optimum microcapsule size range of 500-600 microns in diameter can be achieved without significant compromise in the adequacy of the capsules.

Parameters may be adjusted to decrease the degree of imperfection in the shape of microcapsules, such tailing, which is associated with fibrotic reactions around alginate spheres. One factor that affects the size, shape, and degree of inadequacy in alginate microspheres is the shear stress involved in the encapsulation process. For instance, when shear stresses during the production of alginate spheres are very high, unwanted satellite tiny microartefacts are generated inside and outside of the alginate beads. Certain effects of shear stresses on extruded viscosity non-Newtonian fluids are known. Computational Fluid Dynamics Code (CFD) analysis can be performed to quantify shear stresses in the process and design the process parameters to maintain maximum shear stresses under allowable maximums.

In some instances, fibrotic overgrowths may result in oxygen and nutrient deprivation of the enclosed cells. This problem may be diminished by using purified alginate. Sun Y, Ma X, Ziou D, Vacek I, Sun A M. *Normalization of diabetes in spontaneously diabetic cynomologus monkeys by xenografts of microencapsulated porcine islets without immunosuppression.* J Clin Invest 98: 1417-1422, 1996. Soon-Shiong P. Heintz R E, Merideth N, Yao Q X, Yao Z, Zheng T, Murphy M, Molloney M K, Mendez R, Sandford P A. *Insulin independence in type 1 diabetic patient after encapsulated islet transplantation.* Lancet 343: 950-951, 1994. Hasse C, Zielke A, Klock G, et al. *First successful xenotransplantation of microencapsulated human parathyroid tissue in experimental hypoparathyroidism: long-term function without immunosuppression.* J Microencapsulation 14: 617-626, 1997. Lanza R P, Chick W L. *Transplantation of encapsulated cells and tissues.* Surgery 121:1-9, 1997. De Vos P, Van Straaten J F M, Nieuwenhuizen A G, de Grrot M, Ploeg R J, De Haan B J, Van Schilfgaarde R. *Why do microencapsulated islet grafts fail in the absence of fibrotic overgrowth?* Diabetes 48: 1381-1388, 1999. Zimmermann U. Mimietz Ser M, et al. *Hydrogel-based non-autologous cell and tissue therapy.* BioTechniques 29: 564-581, 2000. In addition to purity, the size, durability, and any imperfections in the shape of the alginate microcapsules may be important factors to be considered in the use of islet microcapsules for transplantation. De Vos P, De Haan B, Wolters G H J, Schilfgaarde R V. *Factors influencing the adequacy of microencapsulation of rat pancreatic islets.* Transplantation 62: 888-893, 1996. De Vos P, De Haan B, Pater J, Schilfgaarde R V, *Association between capsule diameter, adequacy of encapsulation, and survival of microencapsulated rat islet allografts.* Transplantation 62: 893-899, 1996. Lanza R P, Jackson R, Sullivan A, Ringeling J, McGrath C. Kuhntreber W, Chick W L. *Xenotransplantation of cells using biodegradable microcapsules.* Transplantation 67: 1105-1111, 1999. Leblond F A, Simard G, Henley N, et al. *Studies on smaller (~315μ) microcapsules: Feasibility and safety of intrahepatic implantations of small alginate poly-L-lysine microcapsules.* Cell Transplant 8: 327-337, 1999. Darrabie M, Freeman B K, Kendall W F, Hobbs H A, Opara E C. *Durability of polylysine alginate microcapsules.* J Biomed Mater Res 54: 396-399, 2001. In some embodiments, the microencapsulation process involves the formation of gelled alginate spheres containing cells, followed by a first coating with poly-L-lysine, and an outer coating with alginiate to form a semi-perineable membrane around the initial alginate core. Opara E C. *The therapeutic potential of islet cell transplants in the treatment of diabetes.* Expert Opin Investig Drugs 7: 1-11, 1998. Without wishing to be bound by a particular theory, it may be important that the process of outer alginate coating is complete because poly-lysine tends to promote the attaclhment of fibroblasts, which causes capsules to be completely covered by cell growth along with other inflammatory reactions, within one week of transplantation. Fan M-Y, Lum Z-P, Fu X-W, et al. *Reversal of diabetes in BB rats by transplantation of encapsulated pancreatic islets.* Diabetes 39: 519-522, 1990. It appears that poly-L-ornithine may be less immunogenic than poly-L-lysine in preliminary studies. Hobbs H A, Kendall W E, Darrabie M, Collins B, Bridges S, Opara E C. *Substitution of polyornithine for polylysine in alginate microcapsules.* Diabetes 49 (suppl 1): A111, 2000. Moreover, chelation (liquefaction) of the cross-linked alginate core may be necessary for enhanced diffusion of permissible molecules, such as insulin, across the semi-permeable membrane. Garfinkel M R. Harland R C, Opara, EC. *Optimization of the microencapsulated islet for transplantation.* J Surg Res 76: 7-10, 1998. The use of barium as a cross-linking cation may result in oxygen deprivation of encapsulated cells (Sclirezenmeir J, Kirchgessner J, Gero L, et al. *Effect of microencapsulation on oxygen distribution in islets organs.* Transplantation 57: 1308-1314, 1994) because barium-crosslinked alginate microcapsules cannot be liquefied. Zimmermann U, Mimietz Ser M, et al. *Hydrogel-based non-autologous cell and tissue therapy.* BioTechniques 29: 564-581, 2000. Other investigators have shown that increasing the incubation time during the poly-lysine coating can increase the thickness of the poly-lysine membrane, and can reduce the molecular size exclusion of microcapsules. Brissova M, Petro M, Lacik I, Powers A C, Wang T. *Evaluation of microcapsule Permeability via inverse size exclusion chromatography.* Anal Biochem 242: 104-111, 1996.

Mechanical strength and the durability of the microcapsules may also be determined or estimated as part of the optimization process of device parameters. The permeability properties of the microcapsules may be selected using standard pore-size exclusion techniques. Powers A C, Brissova M, Lacik I, et al. *Permeability assessment of capsules for islet transplantation.* Ann NY Acad Sci 831: 208-216, 1997. Various data on these parameters, including data generated with a single needle device, may be used to determine the performance of microcapsules produced according to embodiments of the present invention.

The following non-limiting examples are provided to illustrate embodiments of the present invention in detail. In the following examples, a single cell line rather than a composite tissue of cells, such as the islet, can be used to provide the use of molecular probe techniques for rapid assessment of cell viability after encapsulation.

EXAMPLE 1

Production of Encapsulated Hep G2 Cells

Encapsulated Hep G2 cells may be produced, for example, using the encapsulation device 100 shown in FIG. 1. The encapsulation solution (in the cell/solution suspension 127) is 1.5% ultrapurified sodium alginate (Kelco/Monsanto, San Diego). The post-encapsulation solution 139 is calcium chloride. The wash solution 133 is a saline bath.

EXAMPLE 2

Post-Production Steps and Testing of Encapsulated Hep G2 Cells

The beads may be first coated with about 0.05% to 0.1% poly-ornithine for perme-selectivity, followed by a second coating with about 0.1% to 0.3% alginate. Tests of viability of the encapsulated Hep G2 cells may be performed using the LIVE/DEAD® Viability/Cytotoxicity Kit (L-3224, Molecular Probes, Inc., Eugene, Oreg.) assay. This assay provides a two color fluorescence cell viability assessment that is based on the simultaneous determination of live and dead cells with two probes that measure two recognized parameters of cell viability, namely, intracellular esterase activity and plasma membrane integrity. Fluorescence images obtained after this assay identify dead cells in red, and live cells in green.

EXAMPLE 3

A-Fetoprotein Tests

The cells of Example 2 may be tested using the Enzyme-Linked Immunosorbent Assay [please confirm] (ELISA) technique to show that α-fetoprotein (MW=76,000 KDa), a key protein made by hepatocytes, can be synthesized and excreted to the exterior after culture of encapsulated Hep G2 cells. Naked and microencapsulated Hep G2 cells may be cultured in minimum essential medium (MUM) supplemented with 20% normal rat serum. Samples (0.5 mL) of the culture media may be taken after 1, 2, 3, 4 and 9 days for assay of a-fetoprotein (AFP) using Dot-Blot apparatus (Bio-Rad) with standard procedures. AFP may be detected using rabbit anti-human AFP antibody. The primary antibody may be visualized using HRP-conjugated anti-rabbit antibody and a chemiluminescence kit. Quantities of AFP in the culture media of both naked and encapsulated Hep G2 cells may be measured after a short-term (24-hour) culture.

EXAMPLE 4

Metabolic Activity Tests

Encapsulated isolated rat islets or other encapsulated cells such as those produced in Example 2 may be used to assess the function of microencapsulated cells. The test is based on the assessment of the metabolic activity of the cells in the absence or presence of a metabolic fuel such as glucose, The test may be readily applicable to any cell type for the immediate assessment of cell function. After encapsulating isolated rat islets, capsules containing one islet/capsule may be selected for experiments. Fluorescence intensity increases above basal (no glucose) as oxygen utilization is increased during glucose metabolism by encapsulated islets, thus showing that the encapsulated islets are viable.

EXAMPLE 5

Microencapsulation Procedure

Experiments may be performed with ultrapurified low viscosity high-mannuronic acid alginate (Kelco/Monsanto, San Diego, Calif.). Small droplets (300-500 µm in diameter) of 1.5% alginate with or without Hep G2 cells may be generated in large quantities using the procedures describe in Example 1. More specifically, the microcapsules may be gelled as they drop into a 1.1% calcium chloride solution where they are allowed to incubate for 15 minutes resulting in solid spherical alginate beads, which are then washed in normal saline. These beads may be coated with poly-L-ornithine by incubation in 0.1% solution of this amino acid polymer for 6-20 minutes (varied to manipulate capsule permeability), followed by washing in normal saline. Additional coating of the microcapsules may be performed by incubating them in 0.25% alginate solution for 4 minutes, followed by another saline washing. The initial alginate bead may then be liquefied by incubation in a solution of 55 mM sodium citrate solution for 7 minutes prior to two final washings with saline. Quality control for microcapsules will be performed by visual examination under the microscope and by the measurement of their mechanical strength and durability.

EXAMPLE 6

Determination of Physical Characteristics of Microcapsules

The sizes and numbers of capsules and cells produced using the techniques discussed in Example 5 may be measured using an inverted microscope which is fitted to a Pixera Camera and linked to a computer program (UTHSCSA Image Tool, University of Texas) for determination of the number and size of particles. Also, the shape of capsules, and imperfections in the microcapsules, such as tailing, and cell protrusion through the capsule membrane, can be assessed and photographed using the microscope and its imaging system.

EXAMPLE 7

Determination of Mechanical Strength and Durability of Microcapsules

The mechanical strength of microencapsulated cells produced as described in Example 5 can be evaluated by measurement of the microcapsule resistance to mechanical stress using various procedures. For example, fluorescein isothiocyanate (FITC)-labeled dextran (MW 50-150 kDa) may be microencapsulated as outline above. The microcapsules may then be mixed with 3 mm glass beads and continuously agitated for a fixed duration of time up to 48 hours. The percentage of broken capsules can be calculated by measuring the fluorescence in the supernatant, and in the residual intact capsules following thorough washing in saline prior to dissolution. Another procedure includes a manual method (e.g., handpicking under a stereomicroscope) in which the percentage of broken capsules can be obtained using a ratio of 250 glass beads per 1000 microcapsules. Leblond F A, Tessier J, Halle J-P. *Quantitative method for the evaluation of biomicrocapsule resistance to mechanical stress*. Biomaterials 17: 2097-2102, 1996. The durability of the microcapsules may be determined using in vitro incubations in serum supplemented RPMI 1640 culture medium maintained for periods up to 6 months at 37° C. Hobbs H A, Kendall W F, Darrabie M, Opara E C. *Prevention of morphological changes in alginate microcapsules fob islet xenotransplantation*. J Investig Med 49: 572-575, 2001.

EXAMPLE 8

Functional Viability of Encapsulated Hep G2 Cells

Molecular probes can be used to assess the quality of encapsulated cells to determine cell viability and proliferation, and metabolic techniques can be used for assessment of function. The function of encapsulated Hep G2 cells can be compared with that of unencapsulated cells. In addition, ELISA assays can be used to determine the identity and quantity of specific proteins (albumin, α-fetoprotein, and transferrin) synthesized and exported by encapsulated Hep G2 cells.

EXAMPLE 9

Viability Tests

LIVE/DEAD® Viability/Cytotoxicity Kit assay (L-3224, Molecular Probes, Inc., Eugene, Oreg.) is a fluorescence-based method of assessing cell viability and can be used in place of the Trypan blue exclusion, 51Cr release, and similar methods for determining cell viability and cytotoxicity. Following encapsulation, the viability of the encapsulated cells can be determined by performing the LIVE/DEAD® cell assay immediately after encapsulation using a sample of the capsules, as previously outlined. The ability of the cells to proliferate may be measured by repeating the LIVE/DEAD® assay on aliquots of the encapsulated cells every other day during 7 days of culture, and by performing the cell proliferation assay, as described earlier. A test may be performed that is based on metabolic activity of the cells and linked to oxygen consumption by the encapsulated cells.

EXAMPLE 10

Cell Proliferation Assay

The CellTitre 96RAQueous One Solution Cell proliferation kit (Promega Corporation, Madison, Wis.) assay can be used for the following assessment. This is a colorimetric method for determining the number of viable cells in proliferation or cytotoxicity assays. The kit reagent contains a novel tetrazolium compound [3-(4,5-dimethylthiazol-2-yl)-5-(3-carboxymethoxyphenyl)-2-(4-sulfophenyl)-2H-tetrazolium, inner salt; MTS(a)] and an electron coupling reagent (phenazine ethosulfate; PES). PES has an enhanced chemical stability, which allows it to be combined with MTS to form a stable solution. This assay may be a reliable substitute for the [3H]thymidine incorporation procedure. Cory A H, Owen T C, Barltrop J A, Cory J G. *Use of an aqueous soluble tetrazolium/formazan assay for cell growth assays in culture.* Cancer Commun 3: 207-212, 1991. Riss T L, Moravec R A. *Comparison of MTT, XTT and a novel tetrazolium compound for MTS for in-vitro proliferation and chemosensitivity assays.* Mol Biol Cell (Suppl) 3: 184a, 1992.

EXAMPLE 11

Oxygen Biosensor Test

The following procedure tests the function of encapsulated cells. The principle of this fluorescence assay is based on the ability of live cells to use oxygen, and provides an instant assessment of the metabolic function of cells. Naked (control) and encapsulated cells may be placed in microplates containing the RPMI 1640 culture medium, with sensors (e.g., RD Biosensor system) at the bottom of wells. Oxygen diffuses from the atmosphere into the medium, and is consumed by live cells. As oxygen becomes depleted, the biosensor fluoresces, providing a linear signal that can be directly correlated to cell viability, which may be assigned viability index scores. The scores may be based on the rate of stimulation of oxygen utilization in 11.1 mM glucose medium compared to the rate in the absence of glucose; high=4; good=3; fair=2; poor=1; no oxygen consumption=0. Blank microplates containing the test materials excluding the cells can be set up and used to correct for any background oxygen consumption in the assay system. Sodium sulfite can be used as a positive control for this assay.

An acceptable level of obtained viable cells as determined by the LIVE/DEAD cell assay immediately after encapsulation can be about 80% or greater. The number of viable cells may increase as the duration of culture is increased, which may be indicative of the ability of the cells to proliferate. This phenomenon may be confirmed by the cell proliferation assay. The encapsulated Hep G2 cells may also be shown to be metabolically viable using the Biosensor test of oxygen consumption.

EXAMPLE 12

Determination of Products of Encapsulated Hep G2 Cells

ELISA assays can be performed with culture media obtained after incubation of encapsulated Hep G2 cells, in order to identify and quantify specific proteins synthesized and exported to the exterior of the capsules. Specifically, assays can be performed to determine the ability of the encapsulated Hep G2 cells to synthesize and export such important proteins as albumin (MW=66 KDa), a-fetoprotein (MW=70 KDa) and transferrin (76 KDa), which may be excreted to the exterior of the capsules. Using a routine procedure of microencapsulation, outlined herein, the pore size exclusion limit of the microcapsules may be approximately 75 KDa. The antibodies/kits for measuring these proteins made and secreted by Hep G2 cells are available from Sigma Co. (St. Louis, Mo.). Large molecular weight proteins, such as ceruloplasmin (135 KDa), IgG (150 KDa), fibrinogen (340 KDa) and alpha2-macroglobulin (720 KDa), which are also made by Hep G2 cells, may exceed the pore size limit of microcapsules made under certain conditions. Adjustments may be made in the concentration of the polyornithine solution, as well as the incubation time of the alginate beads in the polyornithine solution, in order to manipulate the pore size of the semi-permeable membrane. Brissova M, Petro M, Lacik I, Powers A C, Wang T. *Evaluation of microcapsule permeability via inverse size exclusion chromatography.* Anal Biochem 242: 104-111, 1996. Powers A C, Brissova M, Lacik I, et al. *Permeability assessment of capsules for islet transplantation.* Ann NY Acad Sci 831: 208-216, 1997. These adjustments may exclude immune cells, but possibly permit the exit of additional products of the encapsulated Hep G2 cells, including small molecular weight immunoglobulins, such as IgG (MW=150 KDa).

Encapsulated Hep G2 cells may be able to synthesize protein in a fashion similar to that of their unencapsulated counterparts. With adjustments in the perme-selectivity of the microcapsule membrane, molecular products (proteins) with molecular weights less than 150 KDa may be efficiently excreted by the encapsulated Hep G2 cells.

Quantitative data may be expressed as mean+standard error, and for comparative data between sets of experiments, data may be normalized per given volume or number of capsules or cells. Statistical evaluation of data requiring multiple comparisons may be performed by an analysis of variance (ANOVA) computer program (GraphPad, San Diego, Calif.) and depending on the outcome of ANOVA, the Bonferroni correction will be used to assess the significance of difference between samples. In comparisons of the significance of the difference between the means of two groups of data, the student's t-test may be used. A value of $p<0.05$ may be accepted as significant.

In the above examples, poly-L-lysine may be replaced with poly-L-ornithine as the semi-permeable coating of the initial alginate bead. When imperfections occur to expose the poly-amino acid membrane of the microencapsulated cell, polyornithine may be less immunogenic than poly-lysine. Hobbs H A, Kendall W F, Darrabie M, Collins B, Bridges S. Opara E C. *Substitution of polyornithine for polylysine in alginate microcapsules.* Diabetes 49 (suppl 1): A111, 2000. Furthermore, coating with poly-ornithine may provide a smaller perme-selectivity for alginate microcapsules, and may result in microcapsules that are less prone to swelling than poly-lysine-coated capsules, thus obviating the need for sodium sulfate-treatment of polyornithine-coated alginate capsules. The inner alginate core of microcapsules may be liquefied to enhance diffusion of oxygen, nutrients, and hormones, for more desirable function of encapsulated islet cells. Garfinkel M R, Harland R C, Opara, EC. *Optimization of the microencapsulated islet for transplantation.* J Surg Res 76: 7-10, 1998. Microcapsule swelling may cause the destruction of hollow polylysine-coated alginate microcapsules by altering their sizes and shape over time [19, 27]. Darrabie M, Freeman B K, Kendall W F, Hobbs HA, Opara E C. *Durability of polylysine alginate microcapsules*. J Biomed Mater Res 54: 396-399, 2001. Hobbs H A, Kendall W F, Darrabie M, Opara E C. *Prevention of morphological changes in alginate microcapsules for islet xenotransplantation*. J Investig Med 49: 572-575, 2001. Microcapsule swelling induced by colloid osmotic pressure may be diminished.

In the drawings and specification, there have been disclosed typical embodiments of the invention and, although specific terms are employed, they are used in a generic and descriptive sense only and not for purposes of limitation, the scope of the invention being set forth in the following claims.

That which is claimed is:

1. A method for the microencapsulation of cells in a device comprising a first chamber for containing a cell-solution suspension; a plate covering one end of the first chamber, the plate having a plurality of apertures; and a second chamber for receiving encapsulated cells, the method comprising:
applying pressure to the cell-solution suspension in the first chamber so that the cell-solution suspension passes through the plurality of apertures in the plate into the second chamber, wherein cells in the cell-solution suspension are encapsulated when the cells pass through the plurality of apertures in the plate, the cell-solution suspension is in direct contact with the plurality of apertures in the plate, and the plurality of apertures and the plate are formed as a single, unitary member.

2. The method of claim 1, wherein applying pressure to the cell-solution suspension comprises forcing compressed air into the first chamber.

3. The method of claim 2, wherein forcing compressed air into the first chamber further comprises forcing a plurality of compressed air pulses into the first chamber.

4. The method of claim 1, wherein applying pressure to the cell-solution suspension comprises actuating a piston to apply pressure to the cell-solution suspension.

5. The method of claim 4, wherein actuating a piston further comprises applying a pulsed force to the piston.

6. The method of claim 1, wherein the cell-solution suspension comprises alginate.

7. The method of claim 1, wherein the second chamber contains a calcium chloride solution.

8. The method of claim 1, wherein the apertures comprise a tapered inlet facing the first chamber and an outlet facing the second chamber.

9. The method of claim 8, wherein the apertures further comprise a channel between the inlet and the outlet, the inlet providing a greater cross-sectional area than the channel for flow between the first and second chamber.

10. The method of claim 8, wherein the outlet has a greater cross-sectional area than the channel.

11. A method for the microencapsulation of cells in a device comprising a first chamber for containing a cell-solution suspension; a plate covering one end of the first chamber, the plate having a plurality of apertures; and a second chamber for receiving encapsulated cells, the method comprising:
applying pressure to the cell-solution suspension in the first chamber so that the cell-solution suspension passes through the plurality of apertures in the plate into the second chamber, wherein cells in the cell-solution suspension are encapsulated when the cells pass through the plurality of apertures in the plate;
wherein the plurality of apertures comprises between about 3000 to about 5000 apertures, each aperture comprising a tapered inlet, the inlet having a cross-sectional diameter of about 0.5 mm at an end adjacent the first chamber; an outlet having a cross-sectional diameter of about 0.5 mm at an end adjacent the second chamber, the inlet and outlet being connected by a channel portion having a cross-sectional diameter of between about 50 µm and about 500 µm.

12. The method of claim 11, wherein applying pressure to the cell-solution suspension comprises actuating a piston to apply pressure to the cell-solution suspension.

13. The method of claim 12, wherein actuating a piston further comprises applying a pulsed force to the piston.

14. The method of claim 11, wherein the cell-solution suspension comprises alginate.

15. The method of claim 11, wherein the second chamber contains a calcium chloride solution.

16. The method of claim 11, wherein the apertures comprise a tapered inlet facing the first chamber and an outlet facing the second chamber.

17. The method of claim 16, wherein the apertures further comprise a channel between the inlet and the outlet, the inlet providing a greater cross-sectional area than the channel for flow between the first and second chamber.

18. The method of claim 16, wherein the outlet has a greater cross-sectional area than the channel.

19. The method of claim 11, wherein the plate and the apertures are formed as a single unitary member.

20. A method for the microencapsulation of cells in a device comprising a first chamber for containing a cell-solution suspension; a plate covering one end of the first chamber, the plate having a plurality of apertures; and a second chamber for receiving encapsulated cells, the method comprising:
applying pressure to the cell-solution suspension in the first chamber so that the cell-solution suspension passes through the plurality of apertures in the plate into the second chamber, wherein cells in the cell-solution suspension are encapsulated when the cells pass through the plurality of apertures in the plate;
wherein the plurality of apertures comprises between about 3000 to about 5000 apertures, each aperture comprising a tapered inlet, the inlet having a cross-sectional diameter of about 0.5 mm at an end adjacent the first chamber; an outlet having a cross-sectional diameter of about 0.5 mm at an end adjacent the second chamber, the inlet and outlet being connected by a channel portion having a cross-sectional diameter of between about 50 µm and about 500 µm and the plate and the apertures are formed as a single unitary member.

* * * * *